(12) United States Patent
Chouaib et al.

(10) Patent No.: US 8,058,252 B2
(45) Date of Patent: Nov. 15, 2011

(54) USE OF INHIBITORS OF SCINDERIN AND/OR EPHRIN-A1 FOR TREATING TUMORS

(75) Inventors: Salem Chouaib, Bourg-la-Reine (FR); Soraya Rifal, Rueil Malmaison (FR); Catherine Gaudin, Savigny-sur-Orge (FR); Fathia Mami-Chouaib, Bourg-la-Reine (FR)

(73) Assignee: Institut Gustave Roussy, Villejuif (FR)

( * ) Notice: Subject to any disclaimer, the term of this patent is extended or adjusted under 35 U.S.C. 154(b) by 79 days.

(21) Appl. No.: 12/159,460

(22) PCT Filed: Dec. 28, 2006

(86) PCT No.: PCT/IB2006/004199
§ 371 (c)(1),
(2), (4) Date: Nov. 14, 2008

(87) PCT Pub. No.: WO2007/080457
PCT Pub. Date: Jul. 19, 2007

(65) Prior Publication Data
US 2009/0156531 A1 Jun. 18, 2009

(30) Foreign Application Priority Data
Dec. 30, 2005 (WO) .................. PCT/EP2005/014229

(51) Int. Cl.
C12N 15/11 (2006.01)
C12N 15/00 (2006.01)
C07H 21/04 (2006.01)
A01N 63/00 (2006.01)

(52) U.S. Cl. .................. 514/44 A; 536/24.5; 435/455; 424/93.21

(58) Field of Classification Search .................. None
See application file for complete search history.

(56) References Cited

U.S. PATENT DOCUMENTS

| 6,184,352 B1 * | 2/2001 | Nakamura et al. | 530/350 |
| 2003/0091569 A1 * | 5/2003 | Gerritsen et al. | 424/146.1 |
| 2004/0029275 A1 * | 2/2004 | Brown et al. | 435/375 |
| 2004/0259247 A1 * | 12/2004 | Tuschl et al. | 435/375 |

OTHER PUBLICATIONS

Carter et al. (2002) Nature Cell Biology 4:565-73.*
Trifaro et al. (2000) Neurochemical Research, vol. 25, No. 1, pp. 133-144.*
Bass (2001) Nature 411:428-9.*
Afroze et al. (2003) Am J Physiol Cell Physiol 285: C88-C95, 2003.*
Lueck et al. (2000) Biochemistry 39: 5274-5279.*
Khong et al (Nature Immunol. 3(11): 999-1005).*
Garcia-Lora (J. Cell. Physiol. 195 :346-345, 2003).*
Otten et al (Leukemia, 2004, vol. 18, pp. 1401-1405).*
Macrae et al. "A conditional feedback loop regulates Ras activity through EphA2" Cancer Cell, 8, pp. 111-118 (2005).
Chen et al. "Inhibition of retinal neovascularization by soluble EphA2 receptor" Experimental Eye Research, 82, pp. 664-673 (2005).
Ogawa et al. "The ephrin-A1 ligand and its receptor, EphA2, are expressed during tumor neovascularization" Oncogene, 19, pp. 6043-6052 (2000).
Lejen et al. "An antisense oligodeoxynucleotide targeted to chromaffin cell scinderin gene decreased scinderin levels and inhibited depolarization-induced cortical F-actin disassembly and exocytosis" J. Neurochem., 76, pp. 768-777 (2001).
Abouzahr et al. "Identification of target actin content and polymerization status as a mechanism of tumor resistance after cytolytic T lymphocyte pressure" PNAS, 103(5), pp. 1428-1433 (2006).
Brantley-Sieders et al. "Ephrin-A1 facilitates mammary tumor metastasis through an angiogenesis-dependent mechanism mediated by EphA receptor and vascular endothelial growth factor in mice" Cancer Research, 66(21), pp. 10315-10324 (2006).

* cited by examiner

*Primary Examiner* — Richard Schnizer
(74) *Attorney, Agent, or Firm* — Morgan, Lewis & Bockius LLP (57) ABSTRACT

The invention relates to the use of inhibitors of the expression or the activity of scinderin and/or of ephrin-A1 inhibitors for increasing the susceptibility of tumor cells to CTL killing. Such inhibitors may be for instance interfering RNAs targeting the scinderin gene and/or interfering RNAs targeting the ephrin-A1 gene.

13 Claims, 6 Drawing Sheets

IGR-Heu

IGR-HeuR8

B

IGR-Heu

IGR-HeuR8

USE OF INHIBITORS OF SCINDERIN AND/OR EPHRIN-A1 FOR TREATING TUMORS

Related Applications

The present application is a U.S. National Phase Application of International Application PCT/IB2006/1004199, filed Dec. 28, 2006, which claims the benefit of PCT/EP2005/014229, filed Dec. 30, 2005, all of which are herein incorporated by reference in their entirety.

The invention relates to methods for increasing the efficiency of cancer immunotherapy, by reducing the resistance of tumor cells to cell-mediated cytotoxicity.

CD8+cytolytic T lymphocytes (CTL) are important effector cells during tumor rejection. This view is supported by a number of experimental (SCHREIBER and FORMAN 1990) and clinical data (BOON et al. 1994). Currently, most attempts at cancer immunotherapy involve the generation of CTLs against tumor-associated antigens (TAA). The identification of these antigens and their T-cell epitopes recognized by autologous T cells has lead to their broad use as immunogens to induce or augment TAA-specific immune responses in vaccination strategies. However, the understanding of tumor-host interactions remains elusive despite this identification. In this respect, tumor rejection in patients does not always follow successful induction of tumor-specific immune responses by cancer vaccine immunotherapy. Evidence has been provided indicating a paradoxical co-existence of cancer cells with TAA-specific immune cells in tumor-competent host. (SHANKARAN et al. 2001; LIU et al 2005). There are increasing indications that tumor cells play a crucial role in the control of immune protection (CHOUAIB et al. 1997) and contain many overlapping mechanisms to maintain their functional disorder and evasion. Furthermore it has been reported by DUNN et al., that tumor specific T cell responses may prevent tumor cell growth, but they may also select for tumor antigen negative and resistant variants in vivo (DUNN et al. 2002; DUNN et al. 2004). It is likely that tumor escape variants will emerge most frequently in the context of effective immunothERAP1es (KHONG and RESTIFO 2002). Clearly, even if a strong and sustained cytotoxic response is induced, complex issues such as tumor evasion and selection of tumor-resistant variants remain.

Even though resistance of tumor cells to cell-mediated cytotoxicity remains a drawback in the immunotherapy of cancer, its molecular basis is poorly understood. A great deal of effort has been focused on trying to understand the tumor escape to immune surveillance and to understand the molecular basis of tumor tolerance (DE BONO et al. 2003; RIMSZA et al. 2004). However, a comprehensive analysis of gene regulation has not yet been performed although several pathways and genes were associated with tumor resistance to CTL killing (BOTS et al 2005; HUANG et al. 2005).

The inventors have now studied the behaviour of tumor cells under CTL selection pressure in vitro. They have observed that this selection pressure induced the selection of tumor cells resistant to CTL-mediated killing, and that the acquisition of resistance was associated with an abnormal CTL/target cell interaction. Electron microscopy analysis revealed that the synapses formed between CTLs and resistant targets appeared clearly much looser with only occasional tight contacts at the CTL/tumor cell interface.

The acquisition of resistance by tumor cells was also associated with a remarkable change in cell morphology as compared to control sensitive cells, accompanied by an alteration in actin polymerization.

It is known that actin cytoskeleton plays a crucial role in various cellular processes, linked to the regulation of cell signalling, apoptosis, NK mediated lysis, and T cell activation (MILLS et al. 1999; ROSEN et al. 2000; WATZL and LONG 2003; SECHI and WEHLAND 2004), and it has been reported that changes in the expression of specific structural components of the cytoskeleton of tumor cells can contribute to tumorigenesis, or may affect their susceptibility to cytotoxic treatments (JANKE et al. 2000; GAJATE and MOLLINEDO 2005). However little is known about the consequence of morphological changes of target cells on CTL-mediated cytotoxicity.

To determine the relationship between morphological changes and resistance to CTL, the inventors analysed the gene expression profile associated with the acquisition of tumor resistance to specific lysis, focusing on actin-related genes. Among the genes that were overexpressed in the resistant variant, they identified in particular scinderin and ephrin-A1.

Scinderin is involved in the control of dynamic changes of actin cytoskeleton networks (RODRIGUEZ DEL CASTILLO et al. 1990); it belongs to the gelsolin superfamily, which comprises several actin binding proteins involved in several cellular functions including cell motility and control of apoptosis (KWIATKOWSKI 1999). Ephrin-A1, a glycosylphosphatidylinositol (GPI)-anchored ligand, has been reported to play a role in the regulation of cytoskeleton organization (BECKMANN et al. 1994) and to be involved in the control of tumor growth (POTLA et al. 2002; IIDA et al 2005).

The inventors have further found that targeting the scinderin and ephrin-A1 genes with siRNA not only reverted cell morphology and F-actin content but also significantly increased the susceptibility of the resistant variants to CTL-induced lysis.

The present invention thus relates to a method for increasing the susceptibility of a tumor target cell to CTL killing wherein said method comprises inhibiting the expression or the activity of scinderin and/or of ephrin-A1 in said target cell.

According to a preferred embodiment, the method of the invention comprises inhibiting the expression or the activity of both scinderin and ephrin-A1.

According to another preferred embodiment, the method of the invention comprises inhibiting the expression of the scinderin gene and/or the expression of the ephrin-A1 gene by RNA interference.

Preferably, the method of the invention comprises contacting said target cell with an interfering RNA selected among:
  a) an interfering RNA targeting the scinderin gene;
  b) an interfering RNA targeting the ephrin-A1 gene;
  c) a combination of a) and b).
or with a DNA precursor (or a combination of DNA precursors) of said interfering RNA(s).

When the interfering RNA targeting the scinderin gene and the interfering RNA targeting the ephrin-A1 gene are used in combination, these RNAs (or their DNA precursors) can be formulated in two separate pharmaceutical compositions, which will be administered either simultaneously or sequentially, through the same route or not, depending on the physician's choice. They can also be associated in a same pharmaceutical composition.

The invention thus provides:
  a pharmaceutical composition comprising an interfering RNA targeting the scinderin gene or a DNA precursor of said interfering RNA;

a pharmaceutical composition comprising an interfering RNA targeting the scinderin gene or a DNA precursor of said interfering RNA;

a pharmaceutical composition comprising an interfering RNA targeting the scinderin gene or a DNA precursor of said interfering RNA, and an interfering RNA targeting the ephrin-A1 gene or a DNA precursor of said interfering RNA.

An interfering RNA is a double-stranded RNA molecule which is able to inhibit in a sequence specific manner, the expression a target gene, by triggering the degradation of its mRNA.

Interfering RNAs suitable for use in mammalian cells should have a double-stranded portion of less than 30 bp, in order to avoid the non-specific interferon response which is induced by longer double-stranded RNA. This includes in particular small interfering RNAs (siRNAs) (ELBASHIR et al. 2001; TUSCHL 2002) and short hairpin RNAs (shRNAs) that are subsequently processed to siRNA by the cellular machinery (PADDISON et al. 2002; YU et al. 2002; SIOLAS et al. 2005). Typically, siARNs have a length from 19 to 25 nucleotides, including a double-stranded portion of 19 to 23 nucleotides; eventually one or both strand(s) has (have) a 3' overhang from 1 to 3 nucleotides.

A DNA precursor of an interfering RNA is a DNA molecule whose transcript can be processed into siRNA in a mammalian cell (for instance a DNA molecule which can be transcribed in shRNA).

Examples of siRNAs targeting the ephrin-A1 gene and the scinderin gene, and allowing to obtain an efficient inhibition of these genes are given below, as SEQ ID NO: 1 and SEQ ID NO: 2. Of course, these sequences are not limitative, and other suitable siRNA sequences can be designed from the available sequences of scinderin and ephrin-A1 genes, using for instance the strategy proposed by JAGLA et al. (2005) or IZQUIERDO (2005).

Once a suitable sequence has been defined, siRNAs, shRNAs, as well as their DNA precursors can be obtained by methods known in themselves, including in particular chemical synthesis and genetic engineering. Various methods for administering interfering RNAs, or DNA precursors thereof, to target cells or tissues are also known in themselves (for review cf. for instance AMARZGUIOUI et al. 2005; SANDY et al. 2005).

The present invention can be used in combination with cellular immunotherapy for the treatment of various tumors. It can also, eventually, be further combined with other anti-tumoral thERAP1es, for instance chemotherapy.

The present invention will be further illustrated by the additional description which follows, which refers to examples of obtention and use of siRNAs and compositions of the invention. It should be understood however that these examples are given only by way of illustration of the invention and do not constitute in any way a limitation thereof.

LEGENDS TO FIGURES

(A) Cytotoxic activity of Heu161 on IGR-Heu autologous LCC cell line and the selected clone IGR-HeuR8. Cytotoxicity was determined by a conventional 4-h $^{51}$Cr release assay at the indicated E:T ratios. Data shown are representative of three independent experiments.

(B) Analysis of MHC class I, TAP and ERAP expression. ERAP1, MHC Class I and TAP-1 were analyzed by immuno-precipitation followed by immunblotting. ERAP1 was detected with mAb 6H9, MHC class I detected with a rabbit polyclonal antibody. TAP-1 was detected with mAb 148.3. Proteasome was detected using mAb MCP21.

Expression of granzyme B (A) and perforin (B) genes in CTL Heu161 after stimulation with the sensitive IGR-Heu cell line or with the resistant IGR-HeuR8 cell clone. Quantitative real time-PCR analysis of RNA isolated from conjugate left for the indicated time (0, 30 min, 2 h, 4 h, 6 h) was performed as described in experimental procedures. Data are representative of three individual experiments.

(B) Lower panel: Resistant targets are observed in close proximity to the CTLs but contact between points is not very close.

Arrowheads: lytic granule; N, nucleus;. The scale bar represents 200 nm.

IGR-Heu and IGR-HeuR8 were plated on glass coverslips and, stained with 568 Alexa Fluor-phalloidin, before analyzis with a Zeiss Axiovert 200 inverted fluorescence microscope. Data are from one representative experiment out of at least three.

(B) Microscopical analysis of synaptic polymerized actin. Tumor cells were incubated with autologous CTL for 30 min at 2:1 ratio. After washing to eliminate nonadherent lymphocytes, conjugates were stained with 568 Alexa Fluor-phalloidin and analyzed with a Zeiss Axiovert 200 inverted fluorescence microscope. Data are from one representative experiment out of at least three for each panel.

72 h after transfection, IGR-HeuR8 were incubated with the CTL. The conjugates were bound to poly-L-lysine-treated coverslips, fixed and stained with 568 Alexa Fluor-phalloidin for visualization of polymerized F-actin. Data are from one representative experiment out of three.

Killing of IGR-HeuR8 by autologous CTL after inhibition of scinderin and ephrin-A1 or the combination of both. 51-Chromium-labeled cells were incubated at 37° C. with CTL at different ratios. After 4 h, the supernatants were collected and analyzed by gamma counter. The results obtained are statistically relevant.

EXAMPLES

Experimental Procedures

Tumor cell lines and CTL clone

The NSCLC tumor cell line, IGR-Heu, was derived from a large cell carcinoma (LCC) of the lung as previously described (ASSELIN-PATUREL et al 1998), and cultured in DMEM/F12 1:1 medium containing 10% heat-inactivated FCS, 1% Ultroser G (Gibco BRL, Life Technologies, Cergy Pontoise, France). Heu161 CTL clone was isolated from autologous tumor-infiltrating lymphocytes as described previously (ECHCHAKIR et al. 2000). The resistant cell line to CTL lysis, IGR-HeuR was derived from IGR-Heu, and was established after 3 months of coculture with the autologous CTL. The cell line was then cloned by limiting dilution and several clones, including IGR-HeuR8, were isolated.

Analysis of MHC Class I, TAP and ERAP Expression

ER-API, MHC Class I and TAP-1 were analyzed by immunoprecipitation followed by immunoblotting. Each cell type was lysed in 50 mM Tris, 150 mM NaCl and 1% Triton X-100, pH 7.9 for 30 min. The supernatant was pre-cleared with Sepharose beads coupled with a non-specific mouse mAb for 3 h at 4° C. Equal amounts of the supernatant were incubated for 1 h at 4° C. with monoclonal antibodies (mab) pre-coupled to Sepharose beads specific for MHC Class I (W6/32) and ERAP1 (4D2)(SAVEANU et al 2005). Anti-TAP-1 mAb (148.3) (MEYER et al. 1994) was also incubated with an equal amount of supernatant for 1 h and was immunoprecipitated with protein G beads for 30 min after incubation with antibody. ERAP1 was detected with mAb 6H9, MHC class I detected with a rabbit polyclonal antibody (RS996-4, kindly provided by N. Tanigaki, Roswell Park Memorial Institute) and TAP-1 was detected with mAb 148.3. ERAP2 and proteasome expression was analyzed in complete cell lysates. Proteasome was detected using mAb MCP21 (kindly provided by G. Niedermann, University Hospital for Radiology, Freiburg, Germany). ERAP2 was detected using mAb 3F5 (SAVEANU et al. 2005).

Cytolytic Activity Assay

The cytotoxic activity of CTL clone was measured by a conventional 4 h $^{15}$Cr-release assay using triplicate cultures in round-bottomed 96-well plates. E:T ratios were 30:1, 15:1, 5:1 and 1:1 on 2000 target cells/well. Percent specific cytotoxicity was calculated conventionally.

Confocal Microscopy

For actin staining, tumor cells and autologous CTL were mixed in a 1:2 target:effector ratio and then plated on poly (L-lysine)-coated coverslips, fixed with 3% formaldehyde/PBS for 10 min, and permealized with 0.1% Triton X-100/PBS for 5 min, followed by blocking with 1% BSA/PBS for 20 min. The fixed cells were stained with Alexa Fluor 568-phalloidin (Molecular Probes). Nucleus was stained with TO-Pro 3 (Molecular Probes). The stained cells were analyzed using a fluorescence microscope (Zeiss).

Electron Microscopy

CTLs and tumor cells on coverslips were fixed with 2.5% glutaraldehyde in 0.1M cacodylate buffer pH 7.4. Cells were post-fixed with 2% $OsO_4$ for 45 min on ice, dehydrated in increasing concentrations of ethanol and embedded in Epon while on coverslips. Ultrathin sections were prepared with a Reichert UltracutS ultramicrotome (Leica, Wien, Austria) and viewed with a TEM CM120 Philips electron microscope (FEI company, Eindoven, The Netherlands) after counterstaining with uranyl acetate.

TaqMan Real-Time Quantitative Reverse Transcription-PCR Analysis

For analysis of granzyme B and perforin induction, T cells were conjugated with tumor cells at a 1:1 ratio during 30 min, 2 h, 4 h, 6 h. RNA extraction was performed with Trizol reagent and followed by Taqman for granzyme B and perforin genes. PCR primers and probe for the gene target were designed by Applied Biosystems and used as the manufacturer's recommendations. The amount of sample RNA was normalized from the amplification of an endogenous control (18S). The relative quantification of the transcripts was derived using the standard curve method (Applied Biosystems User Bulletin 2, ABI PRISM 7700 Sequence Detection system).

Oligo Microarray Technology

Sensitive and resistant cell line total RNA were directly compared using Agilent oligonucleotide dual color technology, running dye swap and duplicate experiments. Probe synthesis and labeling was performed by Agilent's Low Fluorescent Low input Linear Amplification kit. Hybridization was performed on human whole genome 44 k oligonucleotide microarrays (Agilent, Palo Alto Calif.) using reagents and protocols provided by the manufacturer. Feature extraction software provided by Agilent (Version 7.5) was used to quantify the intensity of fluorescent images and to normalize results using the linear and lowess subtraction method. Primary analysis was performed using Resolver software (Rosetta) to identify genes differentially expressed between resistant and sensitive cell lines (IGR-Heu/IGR HeuR8) with a fold change >2 and p Value <$10^{-10}$.

RNA Interference

Gene silencing of scinderin and ephrin-A1 expression was performed using sequence-specific siRNA, purchased from Proligo (Proligo, Boulder, Colo.). Briefly, cells were transfected by electroporation with 50 nM of short interfering RNA in a Gene Pulser Xcell Electroporation System (Bio-Rad; 300V, 500 µF) and then allowed to grow for 72 h. Human ephrin-A1 and scinderin siRNA sequences were:

```
5'-GACACCAAUUGUCAUCAUAAA-3'    (SEQ ID NO: 1)
and

5'-GACACAGCUACUACUACAUCU-3'    (SEQ ID NO: 2)

A siRNA targeting EGFP (CAPLEN et al. 2001):
5'-GCAAGCUGACCCUGAAGUUCAU-3'   (SEQ ID NO: 3)
``` was used as a negative control.

All sequences were evaluated for gene specificity using the National Institutes of Health Blast program.

Results:

Example 1

Figure 1:
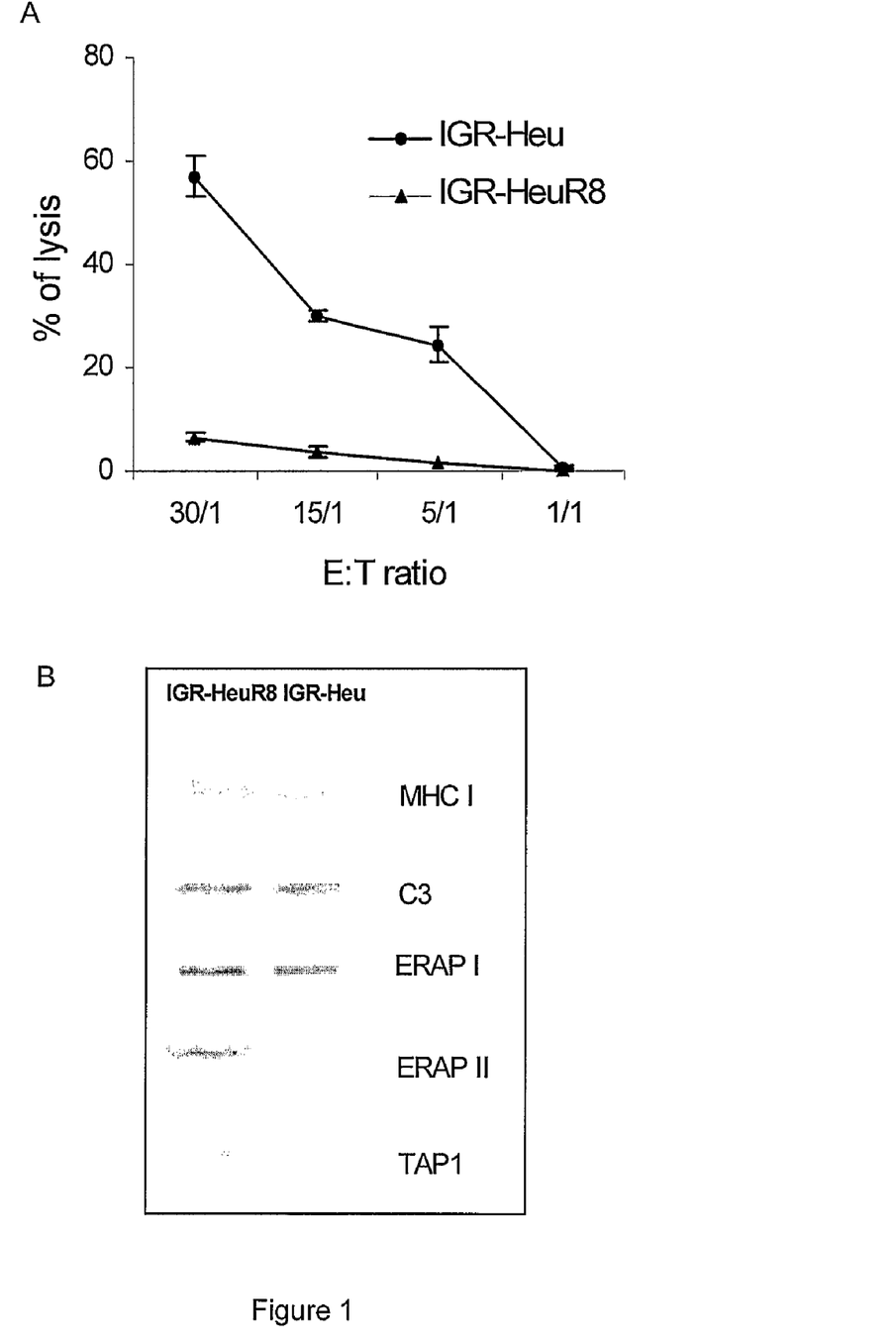
FIG. 1. Phenotypical and functional characterisation of the IGR-HeuR8 resistant clone.

In Vitro CTL Selection Pressure Induces the Selection of Tumor Resistant Variants to Specific Lysis For this study, we have used a human non small cell lung carcinoma (NSCLC) cell line IGR-Heu and the autologous CTL clone Heu161 (CD3+, CD8+, CD4−, CD28−). Heu161 displays a strong cytotoxic activity against IGR-Heu autologous tumor cell line (ECHCHAKIR et al. 2000). Following sustained co-culture of tumor cells with Heu161, a resistant variant line, IGR-HeuR, was established. Using limiting dilution, several resistant variant clones were isolated. Among these resistant variants, IGR-HeuR8 was selected for further studies on the basis of its conserved antigen encoding gene expression (data not shown) and resistance to CTL killing even at high effector/target ratio (FIG. 1A).

Resistance to killing by CTL can be caused by impaired cellular antigen processing and/or presentation. To address this issue, we studied the expression levels of several proteins involved in antigen processing and presentation by HLA class I molecules. Immunoblot analysis (FIG. 1B) revealed equivalent expression levels of the constitutive proteasome subunit C3, of MHC class I heavy chains and of the ER aminopeptidase ERAP1. Expression of the TAP1 peptide transporter subunit, and the second ER peptidase ERAP2 was increased in the resistant cells. Thus impaired antigen processing, as a cause for the resistance of IGR-HeuR8 cells to CTL lysis, is unlikely. In addition, immunofluorescence analysis shows that the expression of MHC class I molecules HLA-A/B/C, HLA B/C, HLA-A2, adhesion molecules ICAM-1, LFA3 and the costimulatory molecule CD86 were similarly expressed by the resistant variant (IGR-HeuR8) and the parental line (IGR-Heu) (data not shown).

Example 2

Figure 2:
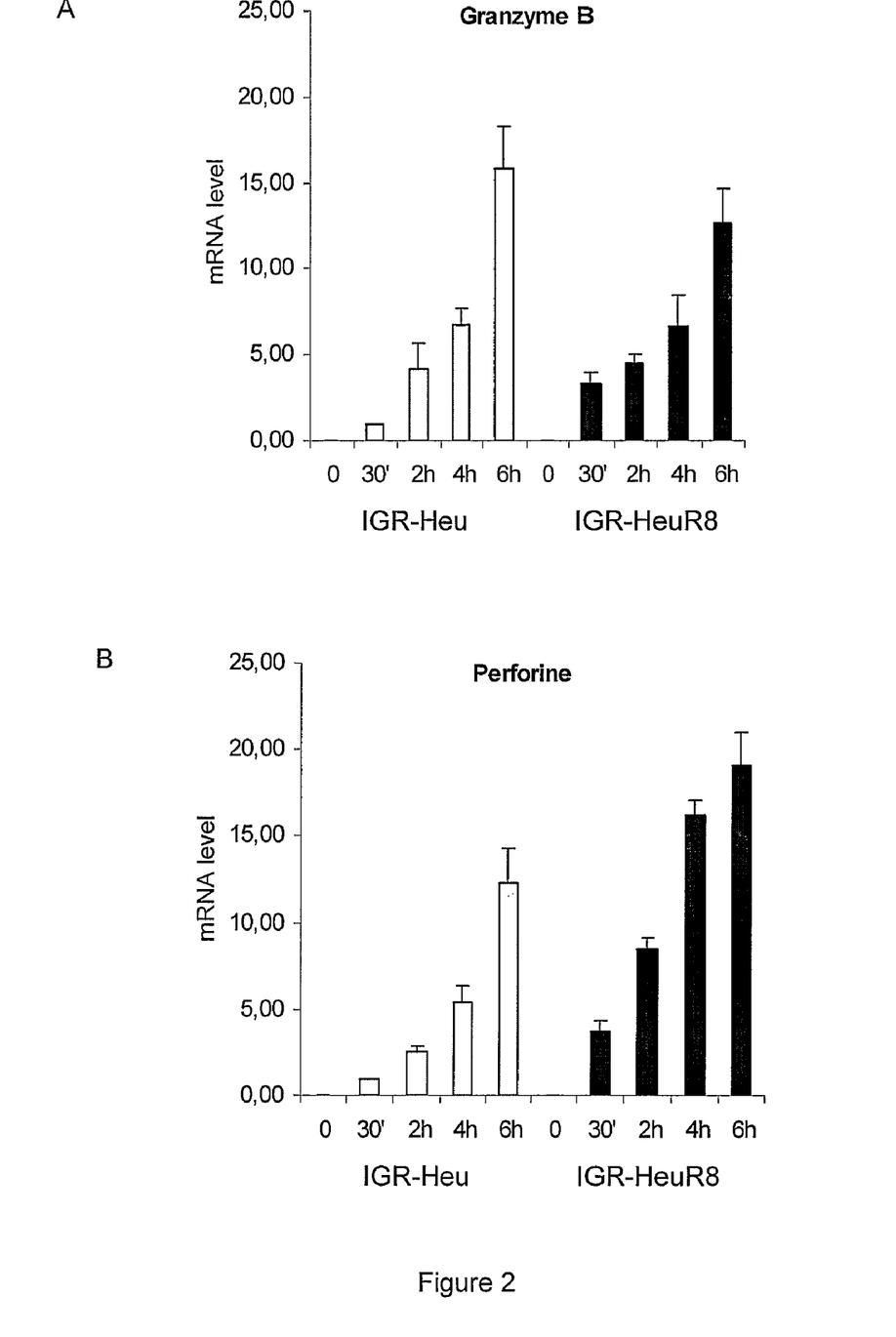
FIG. 2. Transcription and secretion of lytic granules by Heu161 CTL upon stimulation with the sensitive cell line and the derived resistant variant.

The Tumor Resistant Variant Efficiently Induces Granzyme B and Perforin Transcription as Well as Degranulation of the Specific CTL Clone We have previously shown that IGR-Heu cells were defective for Fas/CD95, TRAIL-R1/DR4, TRAIL-R2/DR5 and TNF-R1 death receptor surface expression and that autologous CTL mainly used the secretory pathway to lyse specific target cells (THIERY et al. 2005). To investigate the stimulatory potential of the resistant variant, Heu 161 CTL clone was incubated in the presence of either IGR-Heu parental cell line or the IGR-Heu-R8 resistant variant. Quantitative PCR analysis demonstrated that stimulation of the CTL clone by sensitive and resistant targets resulted in a significant and similar transcription levels of granzyme B (FIG. 2A). Strikingly, a more pronounced transcription of perforin gene was observed when the CTL clone was stimulated with the resistant variant (FIG. 2B). It is also interesting to note that the stimulation of the CTL clone by the parental cell line and the resistant variant induced cytotoxic molecule degranulation as revealed by CD107 induction on the CTL clone surface (data not shown).

Example 3

Figure 3:
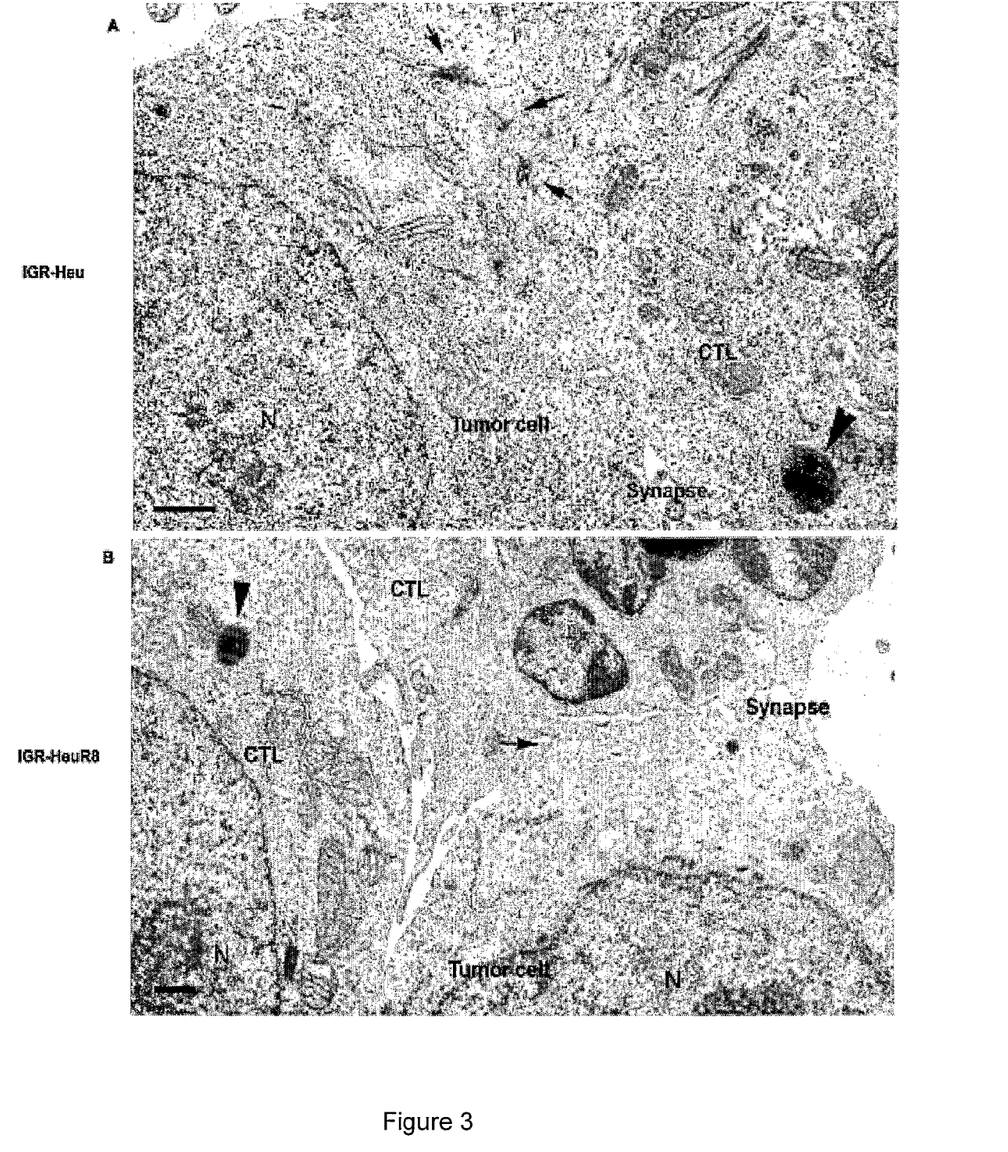
FIG. 3. Electron microscopical analysis of ultra thin sections of CTLs/sensitive and resistant tumor cell conjugates (A) Upper Panel: After 15 min of contact, very close contacts are observed between the sensitive target and the CTL (see arrows for examples). Note the electron dense filaments accumulated at the contact points.

Electron Microscopy Analysis of the Conjugates Formed Between CTLs and Resistant Tumor Cells Reveals a Loosen Synapse Despite the comparable number and the apparent stability of conjugates formed between tumor cells and autologous CTL (data not shown) alteration of the synapse between CTLs and resistant tumor cells may occur. We thus further evaluated synapse formation using electron microscopy. As shown in the FIG. 3A, very close membrane appositions were observed between the CTL clone and the sensitive target, suggesting a very tight interaction. Interestingly, the accumulation of cytoskeletal filaments was evident at these sites of tight apposition (arrows). In contrast, the synapses formed between CTLs and resistant targets appeared much looser with only occasional tight contacts in the synaptic cleft (FIG. 3B). Since CTL-mediated cytotoxicity requires a tight adhesion to the target cell, providing a covered microenvironment for the release of cytotoxic granules, the loosen synapse formed with the tumor cell variant may therefore explain its resistance to CTL killing.

Example 4

The Acquisition of Resistance Involves Target Cell Morphological Change

Figure 4:
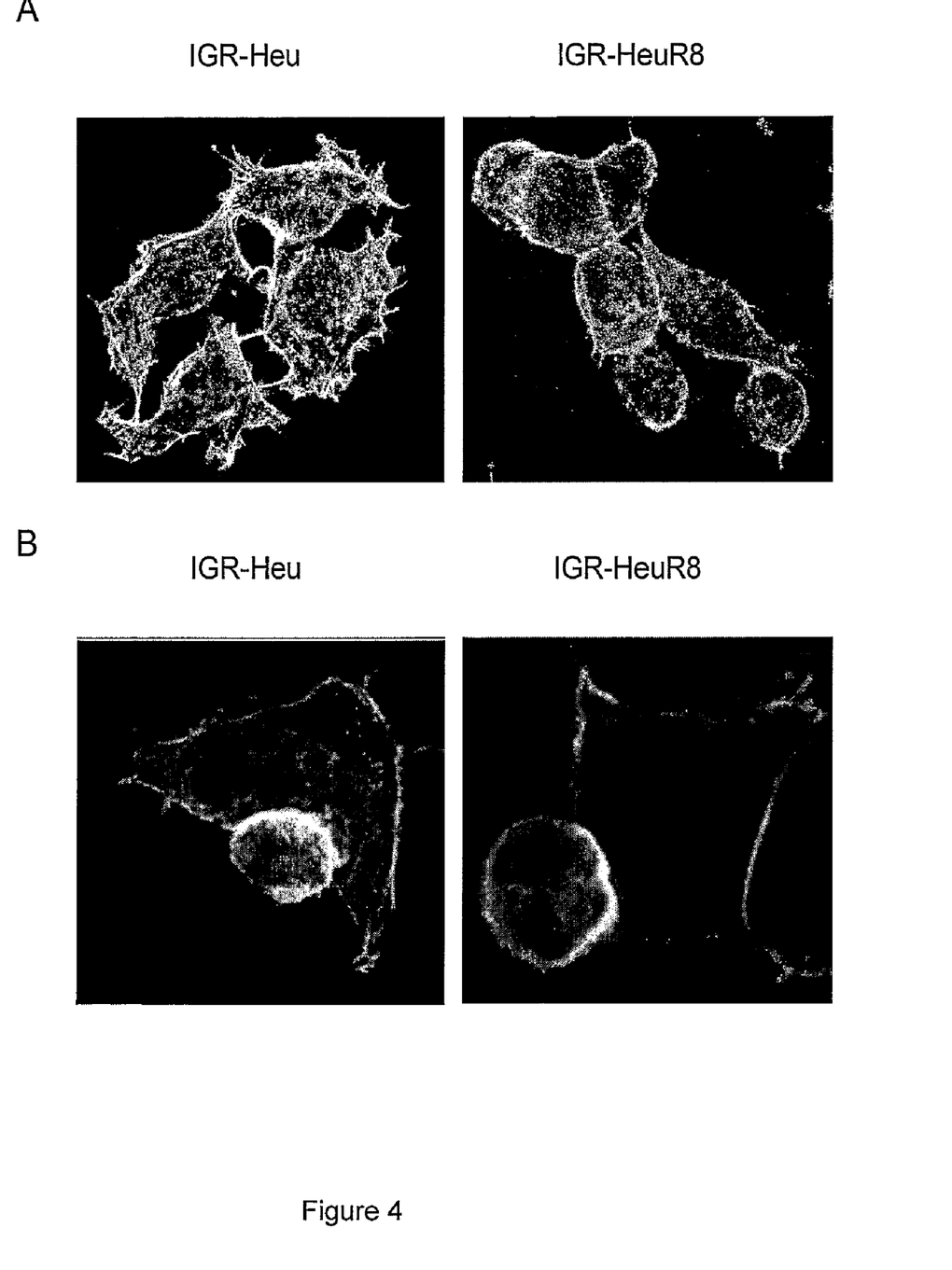
FIG. 4. Analysis of the morphology of resistant variant and conjugate formation with autologous CTL (A) Microscopical analysis of cell morphology.

Data depicted in FIG. 4A show that the acquisition of resistance induced morphological changes in target cells. Indeed, the resistant variant cells acquired a round morphology, with a dramatic reduction of the cells extensions present in the sensitive parental cell line. This was associated with a marked decrease in filamentous actin (F-actin) cellular content, as revealed by Alexa Fluor 568-phalloidin staining, and despite a similar cell size as the sensitive cell line (data not shown). Importantly, actin polymerization at the CTL/resistant target cell synaptic contact was also strongly reduced, as shown in FIG. 4B. This finding indicates that the resistant variant displays a disorganized actin cytoskeleton and that the acquisition of resistance to CTL-mediated killing might result from a shift in the level of actin polymerization. To further examine this hypothesis, sensitive target cells were treated with latrunculin A, an inhibitor of actin polymerization (SPECTOR et al. 1983). Such treatment dramatically inhibited its killing by the CTL clone (data not shown). Moreover, when sensitive cells were incubated with latrunculin A, the level of polymerized actin, as well as their morphology, were comparable to that observed in resistant IGR-HeuR8 (data not shown). These results further support that actin organization is a crucial determinant in the control of target susceptibility to CTL and, accordingly, that changes of the actin cytoskeleton may help tumor cells to escape destruction by CTLs.

Example 5

Ephrin-A1 and Scinderin Overexpression is Associated with Resistant Variant Morphological Change and Altered Susceptibility to CTL Lysis To gain further insight into the molecular mechanisms underlying tumor resistance to specific CTL-mediated cytotoxicity, we have conducted a comprehensive microarray analysis using an Agilent 44 k human oligo microarray. Comparative analysis identified an expression profile of 676 genes that best distinguished resistant variant from parental sensitive target. Functional analysis of transcript profiles identified clusters of genes that were differentially expressed in resistant variant, including a cluster of metabolism, cellular physiological process, cell communication, death, growth and morphogenesis (data not shown).

To determine the relationship between morphological change, resistance to CTL and gene expression profile, we focused on actin-related genes. Two of the most consistently relevant genes, overexpressed in resistant cells, were ephrin-A1 and scinderin. Quantitative RT-PCR results confirmed the direction and magnitude of these gene expression changes. Ephrin-A1 and scinderin increased 45.6 fold and 29.5 fold respectively in the resistant variant as compared to the parental target (data not shown).

Example 6

Figure 5:
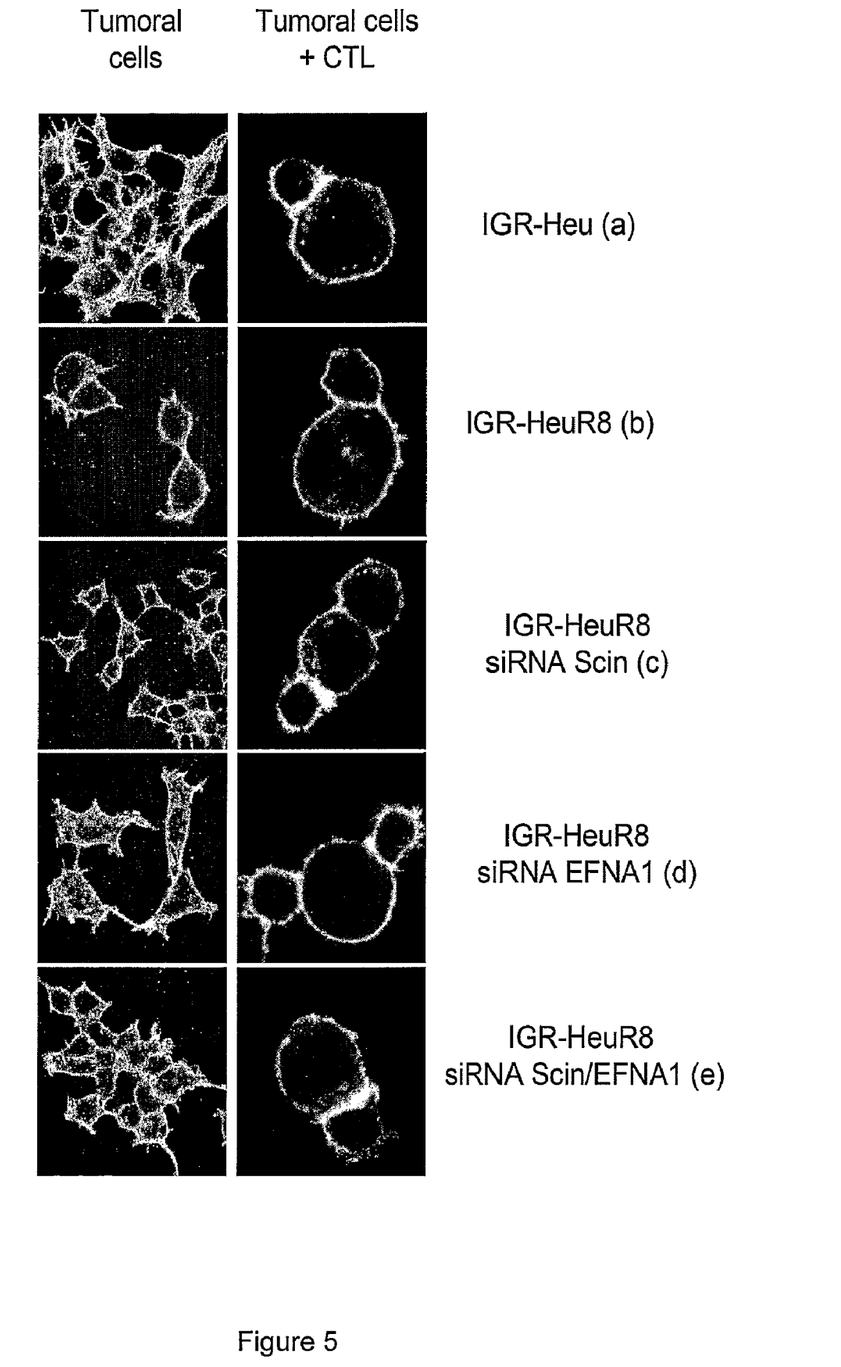
FIG. 5. Morphological consequences of targeting scinderin and ephrinA1
Figure 6:
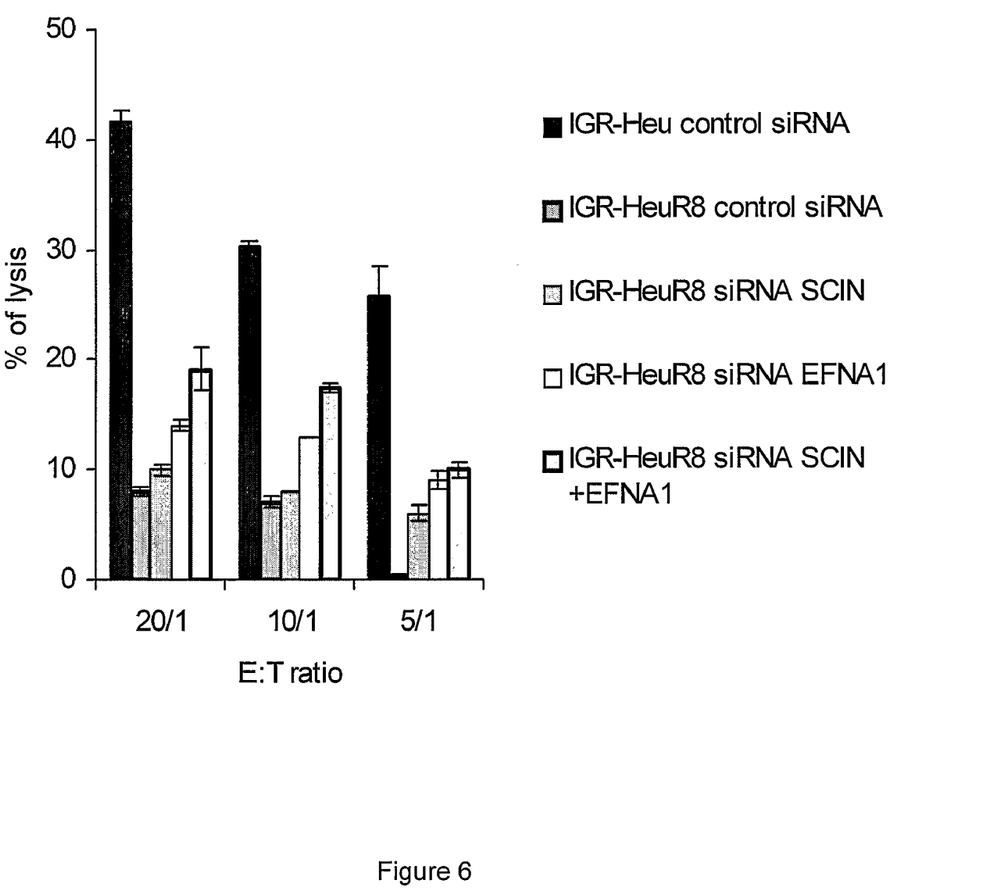
FIG. 6. Functional consequences of targeting scinderin and ephrinA1

RNA Interference-Mediated Silencing of Scinderin and Ephrin-A1 Genes Reverts Resistant Cell Morphology and Increases their Susceptibility to CTL Killing To further assess the putative role of scinderin and ephrin-A1 in the control of tumor variant morphology and susceptibility to CTL-mediated killing, transfection of resistant cells IGR-HeuR8 with siRNAs targeting these genes was performed. A specific and efficient reduction of the levels of ephrin-A1 and scinderin protein by 90%, as compared to a control siRNA, was observed 72 h after the treatment. As shown in FIG. 5, simultaneous knockdown of these genes in the resistant target was accompanied by a striking change in the cell morphology induced upon acquisition of resistance to CTL killing (FIG. 5*b* vs 5*e*), showing that the acquisition of resistance-induced cell rounding was reversible. In addition, phalloidin staining revealed an increase in the cellular F-actin content and actin polymerization at the synaptic contact of siRNA treated cells as compared to the control resistant target (FIG. (FIG. 5b vs 5e). More importantly, while individual knockdown of scinderin and ephrin-A1 resulted in a marginal attenuation of resistance, the simultaneous silencing of both genes significantly increases the sensitivity of the resistant target to CTL killing (FIG. 6).

REFERENCES

AMARZGUIOUI, M., et al (2005). FEBS Lett 579(26): 5974-81.
ASSELIN-PATUREL, C., et al. (1998). Int J Cancer 77(1): 7-12.
BECKMANN, M. P., et al. (1994). Embo J 13(16): 3757-62.
BOON, T., et al. (1994). Annu Rev Immunol 12: 337-65.
BOTS, M., et al. (2005). Blood 105(3): 1153-61.
CAPLEN, N. J., et al. (2001). Proc Natl Acad Sci USA 98(17): 9742-7.
CHOUAIB, S., et al (1997). Immunol Today 18(10): 493-7.
DE BONO, J. S., et al. (2003). Breast Cancer Res 5(3): 154-9.
DUNN, G. P., et al. (2002). Nat Immunol 3(11): 991-8.
DUNN, G. P., et al. (2004). Immunity 21(2): 137-48.
ECHCHAKIR, H., et al. (2000). Int Immunol 12(4): 537-46.
ELBASHIR, S. M., et al. (2001). Nature 411(6836): 494-8.
KWIATKOWSKI, D. J. (1999). Curr Opin Cell Biol 11(1): 103-8.
LIU, K., et al. (2005). Cancer Res 65(10): 4376-88.
MEYER, T. H., et al. (1994). FEBS Lett 351(3): 443-7.
MILLS, J. C., et al. (1999). J Cell Biol 146(4): 703-8.
PADDISON, P. J., et al. (2002). Genes Dev 16(8): 948-58.
POTLA, L., et al. (2002). Cancer Lett 175(2): 187-95.
RIMSZA, L. M., et al. (2004). Blood 103(11): 4251-8.
RODRIGUEZ DEL CASTILLO, A., et al. (1990). Embo J 9(1): 43-52.
ROSEN, K., et al. (2000). J Cell Biol 149(2): 447-56.
SANDY, P., et al. (2005). Biotechniques 39(2): 215-24.
SAVEANU, L., et al. (2005). Nat Immunol.
SCHREIBER, K. L. and FORMAN, J. (1990). J Immunol 144(5): 2018-26.
SECHI, A. S. and WEHLAND, J. (2004). Trends Immunol 25(5): 257-65.
SHANKARAN, V., et al (2001). Nature 410(6832): 1107-11.
SIOLAS, D., et al (2005). Nat Biotechnol 23(2): 227-31.
SPECTOR, I., et al. (1983). Science 219(4584): 493-5.
THIERY, J., et al (2005). J Immunol 174(2): 871-8.
TUSCHL, T. (2002). Nat Biotechnol 20(5): 446-8.
WATZL, C. and LONG, E. O. (2003). J Exp Med 197(1): 77-85.
YU, J. Y., et al. (2002). Proc Natl Acad Sci USA 99(9): 6047-52.

SEQUENCE LISTING

```
<160> NUMBER OF SEQ ID NOS: 3

<210> SEQ ID NO 1
<211> LENGTH: 21
<212> TYPE: RNA
<213> ORGANISM: Homo sapiens

<400> SEQUENCE: 1
gacaccaauu gucaucauaa a                                              21

<210> SEQ ID NO 2
<211> LENGTH: 21
<212> TYPE: RNA
<213> ORGANISM: Homo sapiens

<400> SEQUENCE: 2
gacacagcua cuacuacauc u                                              21

<210> SEQ ID NO 3
<211> LENGTH: 22
<212> TYPE: RNA
<213> ORGANISM: Homo sapiens

<400> SEQUENCE: 3
gcaagcugac ccugaaguuc au                                             22
```

GAJATE, C. and MOLLINEDO, F. (2005). J Biol Chem 280(12): 11641-7.
HUANG, B., et al (2005). Cancer Res 65(12): 5009-14.
IIDA, H., et al. (2005). Gut 54(6): 843-51.
IZQUIERDO, M. (2005). Cancer Gene Ther 12(3): 217-27.
JAGLA, B., et al. (2005). Rna 11(6): 864-72.
JANKE, J., et al. (2000). J Exp Med 191(10): 1675-86.
KHONG, H. T. and RESTIFO, N. P. (2002). Nat Immunol 3(11): 999-1005.

The invention claimed is:

1. A method of increasing the susceptibility of cytolytic T lymphocyte (CTL) resistant tumor cells to cytolytic T lymphocytes in a subject in need thereof, wherein said CTL sensitive tumor cells overexpress scinderin and/or ephrin-A1 relative to CTL sensitive tumor cells of the same lineage, and wherein said method comprises:

administering to the CTL resistant tumor cell a composition comprising an interfering RNA targeting scinderin mRNA, or a DNA encoding said interfering RNA targeting scinderin mRNA; and/or an interfering RNA targeting ephrin-A1 mRNA, or a DNA encoding said interfering RNA targeting ephrin-A1 mRNA.

2. The method of claim 1, wherein said composition comprises a mixture of an interfering RNA targeting scinderin mRNA and an interfering RNA targeting ephrin-A1 mRNA, or a mixture of DNA encoding said interfering RNAs.

3. A pharmaceutical composition comprising an interfering RNA targeting scinderin mRNA or a DNA encoding said interfering RNA, and an interfering RNA targeting ephrin-A1 mRNA or a DNA encoding said interfering RNA.

4. The method of claim 1, wherein the interfering RNA targeting scinderin mRNA, or the DNA encoding said interfering RNA targeting scinderin mRNA comprises the nucleotide sequence as set forth in SEQ ID NO: 2 or complement thereof.

5. The method of claim 1, wherein the interfering RNA targeting ephrin-A1 mRNA, or the DNA encoding said interfering RNA targeting ephrin-A1 mRNA comprises the nucleotide sequence as set forth in SEQ ID NO: 1 or complement thereof.

6. The pharmaceutical composition of claim 3, wherein the interfering RNA targeting scinderin mRNA or the DNA encoding said interfering RNA comprises the nucleotide sequence as set forth in SEQ ID NO: 2 or complement thereof.

7. The pharmaceutical composition of claim 3, wherein the interfering RNA targeting ephrin-A1 mRNA or the DNA encoding said interfering RNA comprises the nucleotide sequence as set forth in SEQ ID NO: 1 or complement thereof.

8. The method of claim 1, wherein the interfering RNA targeting scinderin mRNA, or the DNA encoding said interfering RNA targeting scinderin mRNA; and the interfering RNA targeting ephrin-A1 mRNA, or a DNA encoding said interfering RNA targeting ephrin-A1 mRNA are administered to the tumor cells.

9. The method of claim 1, wherein the interfering RNA targeting scinderin mRNA, or the DNA encoding said interfering RNA targeting scinderin mRNA; or the interfering RNA targeting ephrin-A1 mRNA, or a DNA encoding said interfering RNA targeting ephrin-A1 mRNA are administered to the tumor cells.

10. The method of claim 1, further comprising contacting the tumor cell with a CTL.

11. The method of claim 1, wherein the composition comprises an interfering RNA targeting scinderin mRNA and a DNA encoding an interfering RNA targeting ephrin-A1 mRNA.

12. The method of claim 1, wherein the composition comprises an interfering RNA targeting ephrin A-1 mRNA and a DNA encoding an interfering RNA targeting scinderin mRNA.

13. The method of claim 1, wherein the composition comprises a DNA encoding an interfering RNA targeting scinderin mRNA and a DNA encoding an interfering RNA targeting ephrin-A1 mRNA.

* * * * *